United States Patent [19]

Rao

[11] 4,439,625

[45] Mar. 27, 1984

[54] PRODUCTION OF FORMALDEHYDE

[75] Inventor: Velliyur Nott M. Rao, Wilmington, Del.

[73] Assignee: E. I. Du Pont de Nemours and Company, Wilmington, Del.

[21] Appl. No.: 427,418

[22] Filed: Sep. 29, 1982

[51] Int. Cl.$^3$ .................... C07C 45/29; C07C 47/04
[52] U.S. Cl. .................... 568/473; 568/471; 568/472
[58] Field of Search .................... 568/473, 472, 471

[56] References Cited

U.S. PATENT DOCUMENTS

| 2,462,413 | 2/1949 | Meath | 568/473 |
|---|---|---|---|
| 2,587,468 | 2/1952 | Heider | 260/348.5 |
| 3,948,997 | 4/1976 | Howe et al. | 568/473 |
| 3,959,385 | 5/1976 | Neinburg et al. | 568/454 |
| 3,991,118 | 11/1976 | Diem et al. | 568/454 |
| 4,098,826 | 7/1978 | Alpers et al. | 568/454 |
| 4,167,527 | 9/1979 | Nielsen et al. | 568/473 |
| 4,198,351 | 4/1980 | Branecky et al. | 568/454 |
| 4,219,509 | 8/1980 | Nielsen et al. | 568/473 |
| 4,383,123 | 5/1983 | Ferris et al. | 568/473 |

FOREIGN PATENT DOCUMENTS

| 49-24889 | 6/1974 | Japan | 568/473 |
|---|---|---|---|
| 1272592 | 5/1972 | United Kingdom | 568/473 |
| 1273042 | 5/1972 | United Kingdom | 568/454 |

Primary Examiner—Werren B. Lone

[57] ABSTRACT

A process for converting methanol to formaldehyde at 450° to 750° C. using as catalyst silver, silver-gold alloys or copper-gold alloys in which from 0.001 to 15 parts per million, based on methanol, of phosphorus or phosphorus from a phosphorus compound is present.

8 Claims, No Drawings

PRODUCTION OF FORMALDEHYDE

BACKGROUND OF THE INVENTION

1. Field of the Invention

This invention is concerned with an improvement in the production of formaldehyde from methanol. In particular, it relates to such a process where use of small amounts of phosphorus containing compounds improve selectivity to formaldehyde.

2. Prior Art

The catalytic conversion of methanol to produce formaldehyde has been known since 1878. The use of silver catalysts for such a process has been known since at least 1908 and is disclosed in German Patent No. 228,687. Other metals or metal alloys as well as metal oxides have also been suggested and used for this process.

Commercially there are two processes that are in widespread use. The first utilizes silver as the catalyst. This process is carried out in a methanol rich atmosphere. The second uses a metal oxide catalyst and operates in an oxygen rich atmosphere. Basically the first process is operated at approximately one to three atmospheres absolute, although other pressure ranges can be employed if desired. Methanol and air are passed over a stationary bed of the catalyst. The overall reaction is exothermic in nature and can operate anywhere between 450°–750° C. depending upon process and product requirements. The mixture which is passed through the catalyst bed is not restricted to methanol and air only since various diluents have been disclosed in the literature. Diluents may consist of steam, carbon oxides, and recycled off gases, including formaldehyde.

The mechanism of formaldehyde production is believed to be a combination of two reactions, namely the dehydrogenation and oxidative dehydrogenation of methanol.

$$CH_3OH \rightarrow CH_2O + H_2$$

$$CH_3OH + \tfrac{1}{2}O_2 \rightarrow CH_2O + H_2O$$

Depending upon the conversion required, the silver catalyzed process can be operated in stages. Single stage operation allows only moderate amounts of methanol to be converted in a single pass limited by reaction temperature unless a heat sink such as inerts or water is employed. This necessitates distillation of unreacted methanol from the product formaldehyde and entails substantial investment in distillation facilities.

Another way to operate the process which eliminates distillation or other concentration facilities is to use two or more catalytic stages with interstage cooling. A basic two stage process is disclosed in U.S. Pat. No. 2,462,413 to Meath. An improvement over the Meath process where even lower amounts of methanol in the product can be obtained is disclosed in U.S. Pat. No. 3,959,383 issued to Northheimer.

The use of substantial amounts of trisubstituted organic phosphates and small, but an undetermined amount of phosphine in the production of ethylene oxide from ethylene and air at operating temperatures of ~310° C. using a supported silver catalyst is disclosed in U.S. Pat. No. 2,587,468 issued to R. L. Heider.

SUMMARY OF THE INVENTION

It has been discovered that in the conversion of methanol to formaldehyde, the selectivity of the process to produce formaldehyde is increased when very small amounts of phosphorus containing compounds are co-fed to the reactor. This is observed when the reactor is operated in a single stage with or without added water vapor or in the dual stage where two reactors operate in series. Such selectivity improvement has been demonstrated with silver, silver-gold and copper-gold catalysts.

DETAILED DESCRIPTIN OF THE INVENTION

The present invention pertains to the discovery that use of a very small amount of phosphorus or a phosphorus containing compound in the reactor feed increases selectivity to formaldehyde.

The terms "conversion" and "selectivity" used in the specification, examples and claims are defined as follows:

$$\text{Conversion, mole \%} = \frac{\text{moles methanol converted}}{\text{moles methanol fed}} \times 100$$

$$\text{Selectivity, mole \%} = \frac{\text{moles formaldehyde produced}}{\text{moles methanol converted}} \times 100$$

For the sake of convenience, the phosphorus or phosphorus containing compound may hereafter be sometimes referred to as "moderator" or "catalyst moderator". Moderator or catalyst moderator means in addition to elemental phosphorus, a phosphorus containing compound where the phosphorus is in a formal oxidation state of +3 or +5. The valences for the oxidation states can be satisfied by hydrogen, oxygen, sulfur, hydroxy, thiol, or carbon containing species. The carbon containing species may be aliphatic or aromatic as well as ester functions containing an oxycarbon bond. Obviously, the substituted phosphorus containing compound does not have to be symmetrical since unlike groups can be attached to satisfy the valence requirements.

The preferred method of adding a catalyst moderator to a reactor is to mix it with the methanol vapor inlet steam by direct injection through a jet nozzle or other suitable dispersing device. Alternatively, one can mix it with the methanol prior to vaporization provided decomposition reactions in the vaporizer can be minimized, a phosphorus compound which is soluble in methanol is being used and the boiling point of the moderator is such that known amounts can be vaporized. The former method is preferable when employing a moderator whose boiling point is greater than 100° C. Other methods of moderator introduction will be obvious to those skilled in the art, the only requirement being that the moderator be part of the reaction mixture entering the reactor.

The quantity of the catalyst moderator used is very small. Depending on the particular moderator used the amount of phosphorus it provides will not be greater than 15 ppm, but can be as low as 0.001 ppm (parts per million) both by weight based on the weight of methanol in the reaction mixture. It is not to be construed that the actual catalyst moderator is phosphorus itself since it is not known what happens to phosphorus or a phosphorus containing compound in the immediate vicinity of the catalyst or on the catalyst surface itself. What is known is that these do not permanently stay on the catalyst since the performance of the catalyst reverts back to its original unmoderated state some finite time after moderator addition is stopped. The examples provided refer to parts per million of the moderator used by weight based on the weight of methanol since the effect of molecular structure, association, hydrogen bonding, etc., by themselves or in combination thereof are not precisely known. Therefore, the amount of moderator needed will vary with the type of moderator used but when calculated on a phosphorus basis, the amount of phosphorus they provide will be from 0.001 to 15 ppm by weight, based on the weight of methanol in the reaction mixture. If too much moderator is used, loss of reaction occurs although the effect is not permanent.

The preferred phosphorus compounds are the organophosphites and organophosphates of the formulas

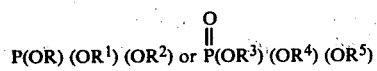

where —R, —R$^1$, —R$^2$, —R$^3$, —R$^4$ and —R$^5$ are the same or different, and selected from the class consisting of alkyl groups containing from 1 to 12 carbon atoms, aryl groups containing from 1 to 12 carbon atoms, alkaryl groups containing from 1 to 12 carbon atoms and —OH.

Such preferred phosphorus containing compounds include trimethyl, triethyl, triisopropyl, tributyl phosphites, and phosphates. As representatives of aryl substituents triphenyl, and tricresyl phosphites and phosphates are preferred. Di- and mono-alkyl and aryl phosphites as well as the completely hydrolyzed acids are also preferred since hydrolysis of organophosphorus compounds is known to result in total hydrolysis or to a mixture of hydrolyzed species depending on the severity of reaction conditions.

In a preferred aspect of the invention from 0.1 to 1.0 mole of water vapor per mole of methanol is present in the feed to the catalyst bed to facilitate hydrolysis of the phosphorus compound.

It is to be understood that the phosphorus can be fed in any form which will convert to an organo phosphorus compound under the reaction conditions, i.e., in the presence of methanol, oxygen (and optionally water vapor) at 450° to 750° C. Thus elemental phosphorus, phosphoric acid, phosphorous acid, PCl$_3$, etc. when added to the reaction system will form the requisite organo phosphorus compounds.

In a typical formaldehyde process, using silver, silver-gold or copper-gold catalyzed reactors, methanol is fed to a vaporizer then to a superheater where the temperature is raised to from about 140° to about 180° C. The superheated methanol is mixed with air and fed to the reactor which is operated at from 450° to 750° C. Optionally the product gases from the reactor can be mixed with additional air and sent to a second reactor to increase conversion of methanol to formaldehyde. The gases finally are sent to an absorber where they are cooled to from 25° to 45° C. Product formaldehyde in water, as 40 to 60% formaldehyde, is removed from the absorber.

The catalysts useful herein are silver, silver-gold alloys containing from 25 to 75 atomic percent silver and the remainder gold, and copper-gold alloys containing from 25 to 75 atomic percent copper and the remainder gold.

The moderators of this invention should find general use in heterogeneously catalyzed oxidation reactions as well, such as the conversion of propylene to acrolein and butadiene to furan.

EXAMPLE 1

A 10 mm (I.D.) quartz tube is filled to a depth of one inch (25.4 mm) with silver crystals which pass a 10 mesh screen and are retained on a 60 mesh screen (Tyler Sieve Series). Methanol, 1.3 g/min., is vaporized and mixed with preheated air to furnish the desired oxygen to methanol ratio reported in Table 1 and passed through the catalyst bed. The catalyst section is heated externally to initiate reaction and once initiated the external heat is adjusted to maintain at the value reported in Table 1. When water vapor is used in the feed in addition to methanol and air, liquid water is vaporized to give the water to methanol ratios reported in Table 1. Triethylphosphite moderator is premixed with the methanol to give moderator levels reported in Table 1 when studying the effect of moderator. The product from the reactor is analyzed by gas chromatography to determine conversion and selectivity. The amount of triethylphosphite (or other moderators) reported in Tables 1 to 8 is based on the amount of methanol fed to the catalyst bed. Runs 1 and 4 are control Runs without moderator. The results are reported in Table 1.

TABLE 1

| Run No | Moderator ppm | Catalyst Bed Temperature °C. | Mole Ratio O$_2$/MeOH | Mole Ratio H$_2$O/MeOH | Conversion MeOH % | Selectivity HCHO % |
|---|---|---|---|---|---|---|
| 1 | 0 | 600 | 0.27 | 0 | 67.0 | 91.5 |
| 2 | 2.5 | 637 | 0.24 | 0 | 55.7 | 92.9 |
| 3 | 5.0 | 669 | 0.28 | 0 | 62.1 | 94.3 |
| 4 | 0 | 606 | 0.312 | 0.50 | 76.3 | 91.0 |
| 5 | 10 | 657 | 0.306 | 0.51 | 67.1 | 94.1 |
| 6 | 15 | 673 | 0.311 | 0.51 | 64.9 | 94.8 |
| 7 | 20 | 685 | 0.302 | 0.52 | 61.2 | 95.3 |

EXAMPLE 2

Example 1 is repeated except trimethylphosphite is used as the moderator in Runs 9, 10, 11 and 12 and trimethylphosphate is used as the moderator in Runs 14 and 15. Runs 8 and 13 are control runs without moderator. The results are reported in Table 2.

TABLE 2

| Run No | Moderator ppm | Catalyst Bed Temperature °C. | Mole Ratio H$_2$O/MeOH | Mole Ratio O$_2$/MeOH | Conversion MeOH % | Selectivity HCHO % |
|---|---|---|---|---|---|---|
| 8 | 0 | 668 | 1.11 | 0.41 | 91.9 | 91.1 |

TABLE 2-continued

| Run No | Moderator ppm | Catalyst Bed Temperature °C. | Mole Ratio H2O/MeOH | Mole Ratio O2/MeOH | Conversion MeOH % | Selectivity HCHO % |
|---|---|---|---|---|---|---|
| 9 | 3.3 | 699 | 1.12 | 0.42 | 90.4 | 92.6 |
| 10 | 6.6 | 707 | 1.14 | 0.42 | 89.2 | 93.4 |
| 11 | 6.6 | 688 | 1.10 | 0.38 | 84.5 | 94.0 |
| 12 | 6.6 | 638 | 0.51 | 0.31 | 75.7 | 93.4 |
| 13 | 0 | 585 | 0 | 0.239 | 64.4 | 91.3 |
| 14 | 15 | 605 | 0 | 0.235 | 59.3 | 93.3 |
| 15 | 30 | 659 | 0 | 0.241 | 56.3 | 94.5 |

EXAMPLE 3

Two 10 mm (I.D.) quartz tubes are filled to a depth of one inch (25.4 mm) with silver crystals as described in Example 1. The two tubes are connected in series with provision to add air to the effluent from the first tube prior to entering the second tube. The reaction in the first tube is initiated with methanol (1.3 g/min.) and air as described in Example 1. The reaction in the second tube is initiated with product from the first reactor and additional air. Both tubes have external heaters around the catalyst section. After reaction is initiated these heaters are adjusted to maintain the values reported for two-stage operation. The product from the second stage is analyzed by gas chromatography to determine conversion and selectivity. The amount of moderator is based on the amount of methanol fed to the first catalyst bed. Runs 16, 17, 23 and 26 are control runs without moderator. In runs 18, 19 and 27 the moderator is trimethylphosphite. In runs 20, 21 and 22 the moderator is triethylphosphite. In runs 24 and 25 the moderator is tri-n-butylphosphite. The results are reported in Table 3.

TABLE 3

| Run No. | Moderator ppm | Catalyst Bed Temp Bed 1 °C. | Catalyst Bed Temp Bed 2 °C. | Mole Ratio overall O2/MeOH | Conversion overall MeOH % | Selectivity overall HCHO % |
|---|---|---|---|---|---|---|
| 16 | 0 | 607 | 650 | 0.46 | 97.9 | 86.5 |
| 17 | 0 | 598 | 653 | 0.47 | 98.4 | 85.4 |
| 18 | 6.6 | 647 | 662 | 0.49 | 94.5 | 93.1 |
| 19 | 6.6 | 662 | 690 | 0.54 | 98.6 | 92.4 |
| 20 | 5.0 | 630 | 649 | 0.47 | 93.5 | 92.3 |
| 21 | 5.0 | 636 | 678 | 0.49 | 96.9 | 92.1 |
| 22 | 5.0 | 642 | 681 | 0.52 | 99.0 | 90.9 |
| 23 | 0 | 604 | 660 | 0.45 | 98.3 | 84.8 |
| 24 | 6.0 | 610 | 676 | 0.48 | 97.8 | 89.3 |
| 25 | 12.0 | 632 | 690 | 0.50 | 97.8 | 91.1 |
| 26 | 0 | 585 | 650 | 0.46 | 98.1 | 86.3 |
| 27 | 3.3 | 632 | 683 | 0.50 | 98.5 | 90.4 |

EXAMPLE 4

Example 3 is repeated except crystals of a copper and gold alloy in a one to one atomic ratio are used as the catalyst and trimethylphosphite is used as the moderator in Runs 29, 30, 32 and 33. Runs 28 and 31 are a control run without moderator. The results are reported in Table 4.

TABLE 4

| Run No. | Moderator ppm | Catalyst Bed Temp Bed 1 °C. | Catalyst Bed Temp Bed 2 °C. | Mole Ratio overall O2/MeOH | Conversion overall MeOH % | Selectivity overall HCHO % |
|---|---|---|---|---|---|---|
| 28 | 0 | 618 | 673 | 0.47 | 89.1 | 86.2 |
| 29 | 3.3 | 628 | 675 | 0.47 | 89.4 | 87.4 |
| 30 | 6.6 | 626 | 672 | 0.47 | 90.0 | 87.6 |
| 31 | 0 | 624 | 675 | 0.45 | 91.4 | 85.0 |
| 32 | 3.3 | 625 | 670 | 0.45 | 89.8 | 88.2 |
| 33 | 13.2 | 643 | 656 | 0.48 | 90.8 | 89.0 |

EXAMPLE 5

Example 3 is repeated except the catalyst bed in the second quartz tube is crystals of a silver-gold alloy (70/30 atomic ratio). The moderator in Runs 35 and 36 is triethylphosphite. Run 34 is the control run without moderator. The results are reported in Table 5.

TABLE 5

| Run No. | Moderator ppm | Catalyst Bed Temp Bed 1 °C. | Catalyst Bed Temp Bed 2 °C. | Mole Ratio overall O2/MeOH | Conversion overall MeOH % | Selectivity overall HCHO % |
|---|---|---|---|---|---|---|
| 34 | 0 | 602 | 595 | 0.44 | 98.6 | 85.3 |
| 35 | 2.0 | 611 | 627 | 0.46 | 98.7 | 87.9 |

TABLE 5-continued

| Run No. | Moderator ppm | Catalyst Bed Temp Bed 1 °C. | Catalyst Bed Temp Bed 2 °C. | Mole Ratio overall O2/MeOH | Conversion overall MeOH % | Selectivity overall HCHO % |
|---|---|---|---|---|---|---|
| 36 | 4.0 | 597 | 605 | 0.45 | 97.8 | 88.7 |

EXAMPLE 6

Example 1 is repeated except dimethylphosphite is injected into the methanol vapors in Runs 38 and 39 rather than being premixed with the methanol. Water is not used. Run 37 is the control run without moderator. The results are reported in Table 6.

TABLE 6

| Run No. | Moderator ppm | Catalyst Bed Temp °C. | Mole Ratio O2/MeOH | Conversion MeOH % | Selectivity HCHO % |
|---|---|---|---|---|---|
| 37 | 0 | 598 | 0.24 | 62.9 | 91.4 |
| 38 | 1.5 | 609 | 0.23 | 59.5 | 92.7 |
| 39 | 3.0 | 620 | 0.24 | 57.1 | 93.5 |

EXAMPLE 7

The use of a moderator is tested in a two-stage process where both reactors are one inch (25.4 mm) in diameter. The operation is similar to Example 3 except that the amount of methanol fed is 7.0 g/min. and trimethylphosphite moderator is directly injected into the gaseous product stream from the first-stage reactor before entering the second stage. Run 40 is a control without moderator and run 41 is with moderator, the amount of moderator being based on the amount of methanol fed to the first reactor. The results are reported in Table 7.

TABLE 7

| Run No. | Moderator ppm | Conversion overall MeOH % | Selectivity overall HCHO % |
|---|---|---|---|
| 40 | 0 | 98.1 | 83.1 |
| 41 | 0.05 | 98.3 | 86.0 |

EXAMPLE 8

Example 1 is repeated except triphenylphosphite is used as the moderator in Runs 43 and 44, phosphorus acid dissolved in methanol in Run 46 and dimethyl methyl phosphonate in Run 47. All these moderators are directly injected into the methanol vapor stream. In Run 49 phosphorus acid dissolved in water is directly injected into the methanol stream. Runs 42, 45 and 48 are controls without moderator. The results are reported in Table 8.

TABLE 8

| Run No. | Moderator ppm | Catalyst Bed Temp °C. | Mole Ratio O2/MeOH | Conversion MeOH % | Selectivity HCHO % |
|---|---|---|---|---|---|
| 42 | 0 | 600 | 0.251 | 67.8 | 91.6 |
| 43 | 3.0 | 600 | 0.236 | 63.6 | 92.6 |
| 44 | 4.5 | 620 | 0.256 | 60.8 | 93.1 |
| 45 | 0 | 601 | 0.264 | 65.1 | 91.4 |
| 46 | 4.0 | 608 | 0.252 | 61.8 | 92.1 |
| 47 | 4.0 | 608 | 0.253 | 62.4 | 92.4 |
| 48 | 0 | 603 | 0.253 | 65.2 | 91.5 |
| 49 | 8.0 | 627 | 0.260 | 59.1 | 94.3 |

I claim:

1. An oxidation process comprising contacting methanol in the presence of oxygen with a catalyst comprising silver, silver-gold alloys or copper-gold alloys, at from 450° to 750° C. wherein from 0.001 to 15 parts per million, based on methanol, of phosphorus from a phosphorus source is present in the reaction mixture entering the reactor and recovering formaldehyde.

2. The process of claim 1 wherein the phosphorus source is injected into the methanol vapor prior to contacting the catalyst.

3. The process of claim 2 wherein the phosphorus source is in the form of

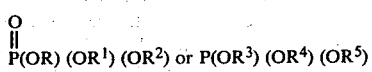

wherein —R, —R$^1$, —R$^2$, —R$^3$, —R$^4$ and —R$^5$ are the same or different and are selected from the class consisting of alkyl groups containing from 1 to 12 carbon atoms, aryl groups containing from 1 to 12 carbon atoms, alkaryl groups containing from 1 to 12 carbon atoms and —OH.

4. The process of claim 3 wherein from 0.1 to 1.0 mole of water vapor is present per mole of methanol in the feed to the catalyst.

5. The process of claim 4 wherein from 0.01 to 5 parts per million, calculated as phosphorus, based on methanol, from the phosphorus source is present.

6. The process of claim 5 wherein the catalyst is silver.

7. The process of claim 5 wherein the catalyst is a gold-silver alloy containing from 25 to 75 mole % gold and the remainder silver.

8. The process of claim 5 wherein the catalyst is a copper-gold alloy containing from 25 to 75 mole % copper and the remainder gold.

* * * * *